US007008380B1

(12) United States Patent
Rees et al.

(10) Patent No.: US 7,008,380 B1
(45) Date of Patent: Mar. 7, 2006

(54) AUTOMATIC LUNG PARAMETER ESTIMATOR

(76) Inventors: Stephen Edward Rees, Forchhammersvej 40, DK-9000 Aalborg (DK); Egon Steen Toft, Blegdalsparken 102, DK-9000 Aalborg (DK); Per Thorgaard, Leonorevej 6, DK-9000 Aalborg (DK); Soren Christensen Kjaergaard, Nordvestvej 11, DK-9000 Aalborg (DK); Steen Andreassen, Kong Georgs Vej 7, DK-9000 Aalborg (DK)

( * ) Notice: Subject to any disclaimer, the term of this patent is extended or adjusted under 35 U.S.C. 154(b) by 0 days.

(21) Appl. No.: 09/890,801

(22) PCT Filed: Feb. 1, 2000

(86) PCT No.: PCT/DK00/00040

§ 371 (c)(1),
(2), (4) Date: Oct. 30, 2001

(87) PCT Pub. No.: WO00/45702

PCT Pub. Date: Aug. 10, 2000

(30) Foreign Application Priority Data

Feb. 3, 1999 (DK) .............................. 1999 00129
May 12, 1999 (DK) .............................. 1999 00649
Jun. 17, 1999 (DK) .............................. 1999 00859

(51) Int. Cl.
*A61B 5/00* (2006.01)
(52) U.S. Cl. .................................. 600/532; 128/204.23
(58) Field of Classification Search ................. 600/322, 600/323, 529–538; 128/204.23
See application file for complete search history.

(56) References Cited

U.S. PATENT DOCUMENTS 4,354,488 A    10/1982    Bartos
(Continued)

FOREIGN PATENT DOCUMENTS

DE    251706    11/1987
(Continued)

OTHER PUBLICATIONS

Andreassen, S., Egeberg, J., Schroter, M.P., Andersen, P.T. (1996). Estimation of pulmonary diffusion resistance and shunt in an oxygen status model. Comput Methods Programs Biomed, vol. 51, pp. 95-105.

(Continued)

*Primary Examiner*—Robert L. Nasser
(74) *Attorney, Agent, or Firm*—Birch, Stewart, Kolasch & Birch, LLP

(57) ABSTRACT

A device for determining one or more respiratory parameters relating to an individual is disclosed, as well as a method for determining one or more respiratory parameters by means of the device, wherein the individual is suffering from hypoxemia or is at risk of hypoxemia. However, the method and the device may also be applied to healthy individual e.g. for testing of medicaments. The device is controlled by a computer equipped with suitable software and includes functionality for on-line continuous data collection, automatic assessment of the timing of measurements, automatic assessment of the next target (oxygen saturation of arterial blood (SpO2)), automatic assessment of the appropriate fraction of oxygen in inspired gas (FIO2) settings to achieve the target SpO2, automatic control of the FIO2, on-line parameter estimation, and automatic assessment of the number of measurememts requied.

58 Claims, 10 Drawing Sheets

U.S. PATENT DOCUMENTS

| | | | |
|---|---|---|---|
| 5,103,814 A | | 4/1992 | Maher |
| 5,237,990 A | | 8/1993 | Psaros et al. |
| 5,251,632 A | * | 10/1993 | Delpy ................. 600/323 |
| 5,282,464 A | | 2/1994 | Brain |
| 5,353,788 A | * | 10/1994 | Miles ................ 128/204.23 |
| 5,365,922 A | * | 11/1994 | Raemer ............ 128/204.23 |
| 5,388,575 A | | 2/1995 | Taube |
| 5,429,123 A | * | 7/1995 | Shaffer et al. ..... 128/204.23 |
| 5,596,986 A | | 1/1997 | Goldfarb |
| 5,682,877 A | * | 11/1997 | Mondry ............ 128/204.23 |

FOREIGN PATENT DOCUMENTS

| | | |
|---|---|---|
| EP | 0342443 | 11/1989 |
| EP | 0502270 | 9/1992 |
| EP | A1502270 | 9/1992 |
| EP | 0753320 | 1/1997 |
| EP | A1753320 | 1/1997 |
| FR | 2599977 | 12/1987 |
| GB | 209321 B | 8/1982 |

OTHER PUBLICATIONS

Andreassen, S., Rees, S.E., Kjaeraard, S., Thorgaard, P., Winter, S.M., Morgan, C.J., Alstrup, P., and Toft, E. (1999). Hypoxemia after coronary bypass surgery modeled by resistance to oxygen diffusion. Critical Care Medicine, vol. 27, pp. 2445-2453.

De Gray, L., Rush, E.M., Jones, J.G. (1997). A non-invasive method for evaluating the effect of thoracotomy on shunt and ventilation perfusion inequality. Anaesthesia, vol. 52, pp. 630-635.

King, T.K.C., Weber, B. Okinaka, A., Friedman, S.A., Smith, J.P. Briscoe, W.A. (1974). Oxygen transfer in catastrophic respiratory failure. Chest, vol. 65, pp. 40S-44S.

Rees, S.E., Rutledge, G.W., Andersen, P.T., Andreassen, S. (1997). Are alveolar block and ventilation-perfusion mismatch distinguishable in routine clincal data. In: Proceedings of the European society of computers in anaesthesia and intensive care conference, Erlangen, Germany, Sep. 18-19, 1997.

Riley, R.L., Counard, A. (1951a) Analysis of factors affecting partial pressure of oxygen and carbon dioxide in gas and blood of the lungs: Theory. J. Applied Physiol., vol. 4, pp. 77-101.

Riley, R.L., Counard, A., Donald, K.W. (1951b). Analysis of factors affecting partial pressure of oxygen and carbon dioxide in gas and blood of the lungs: Method. J. Applied Physiol., vol. 4, pp. 102-120.

Roe, P.G., Galdelrab, R., Sapsford, D., Jones, J.G. (1997). Intra-operative gas exchange and post-operative hypoxaemia. European Journal of Anaesthesiology, vol. 14, pp. 203-210.

Sapsford, D.J., Jones, J.G. (1995). The PiO2 vs. SpO2 diagram: a non-invasive measure of pulmonary oxygen exchange. European Journal of Anaesthesiology, vol. 12, pp. 369-374.

Siggaard-Andersen, M., Siggaard-Andersen, O. (1995). Oxygen status algorithm, version 3, with some applications, Acta Anaesthesiol Scand. vol. 39, Supp. 107, pp. 13-20.

Wagner, P.D., Saltzman, H.A., West, J.B. (1974). Measurement of continuous distributions of ventilation-perfusion ratios: theory. J. Appl. Physiol. vol. 36 (5) :588-599.

Wagner, P.D., Hendenstierna, G., Bylin, G. (1987). Ventilation-perfusion inequality in chronic asthna. Am. Rev. Respir. Dis., vol. 136, pp. 605-612.

* cited by examiner

AUTOMATIC LUNG PARAMETER ESTIMATOR

This application is the national phase under 35 U.S.C. § 371 of PCT International Application No. PCT/DK00/00040 which has an International filing date of Feb. 1, 2000, which designated the United States of America and was published in English.

The present invention relates to a device for determining one or more respiratory parameters relating to an individual. The device may include functionality for on-line continuous data collection, automatic assessment of the timing of measurements, automatic assessment of the next target (oxygen saturation of arterial blood ($SpO_2$)), automatic assessment of the appropriate fraction of oxygen in inspired gas ($FIO_2$) settings to achieve the target $SpO_2$, automatic control of the $FIO_2$, on-line parameter estimation, and automatic assessment of the number of measurements required. This functionality is achieved through a novel device including ventilatory equipment, blood gas analysis equipment and computer hardware and software.

Furthermore, the present invention relates to a method for determining one or more respiratory parameters by means of the above-mentioned device, wherein the individual is suffering from hypoxemia or is at risk of hypoxemia. The individual may also be a healthy individual.

The use of the device for examination and monitoring respiratory parameters relating to humans are of particular interest, but the device may also be applied to farm animals such as pigs, or to domestic animals such as dogs.

BACKGROUND

Oxygen enters the body with inspiration and diffuses from the lungs into the blood. Subsequently the blood circulation transports oxygen to the tissues. Disorders of oxygen transport from the inspired air into the blood can result in a low oxygen saturation of the blood. These disorders in oxygen uptake include abnormal ventilation of the lung, seen in for example chronic obstructive pulmonary disease; abnormal oxygen diffusion in the lung, seen in for example pulmonary fibrosis; and abnormal perfusion (i.e. blood flow) through the lung. Estimation of parameters describing these oxygenation problems is important for diagnosis, monitoring and assessing appropriate therapeutic intervention. This is true in a wide variety of patients, from those who are automatically ventilated and who often require continuous supplement of oxygen, to out-patients who only suffer from dyspnoe during exercise.

In clinical practice the clinician usually relies upon simple measurements or variable estimates to assess the patients oxygenation problems. These include qualitative estimates obtained from stethoscopy or chest X-ray. They also include more quantitative estimates such as arterial oxygen saturation, the alveolar-arterial oxygen pressure gradient, or estimates of the "effective shunt", a parameter which describes all oxygenation problems in terms of a fraction of blood which does not flow through the lungs (Siggaard-Andersen and Siggaard-Andersen, 1985).

Whilst the "effective shunt" is a parameter which has been used widely in the clinical literature it cannot adequately describe the 'clinical' picture seen in patients when the inspired oxygen fraction is varied. This observation is illustrated in FIG. 1 where the "effective shunt" has been estimated for a single patient at four different inspired oxygen fractions, and varies from 15–25%.

In contrast to the poor clinical description of oxygenation problems, detailed experimental techniques such as the Multiple Inert Gas Elimination Technique (MIGET) (Wagner et al., 1974) have been developed which describe the parameters of models with as many as fifty lung compartments. The parameters of these models give an accurate physiological picture of the patient. Whilst the MIGET has found widespread application as an experimental tool its use as a routine clinical tool has been somewhat limited (Wagner et al., 1987). This is largely due to the cost and complexity of the technique.

As stated previously, "effective shunt" is insufficient to describe oxygenation problems. Further parameters describing the patient's oxygenation problem can be obtained from data where inspired oxygen is varied, i.e. data similar to that presented in FIG. 1. This was first recognised by Riley et al. (1951a, 1951b) and later by King et al. (1974). These authors used mathematical models to divide the oxygenation problem into that due to an alveolar-lung capillary drop in the partial pressure of oxygen, and that due to a shunt problem. To estimate two parameters describing the oxygenation problem requires taking measurements of blood samples and of ventilatory variables at each inspired oxygen fraction. Estimating lung parameters using the data from four inspired oxygen fractions required four blood samples, a procedure which is still rather time consuming and in some environments impractical.

More recently, development of non-invasive methods for measuring the oxygen saturation of the blood have lead to renewed interest in estimation of parameters describing oxygen transport obtained by varying $FIO_2$. Andreassen et al. (1996, 1999), Sapsford et al. (1995), de Gray et al. (1997) and Roe et al. (1997), have presented the use of two parameter mathematical models of oxygen transport, the oxygenation problem being described as shunt combined with either a diffusion abnormality (Andreassen et al. (1996, 1999)) or due to a ventilation/perfusion ($\dot{V}/\dot{Q}$) mismatch (Sapsford et al. (1995), de Gray et al (1997), Roe et al., (1997)). These model representations have been shown to provide identical fits to routine blood gas and ventilatory data obtained by varying $FIO_2$ (Rees et al. 1997).

The clinical relevance of the two parameter models is illustrated in FIG. 2, where increases in the pulmonary shunt parameter results in a vertical depression of the $FIO_2/SaO_2$ curve, (V-shift) and abnormalities in the second parameter (ventilation/perfusion ($\dot{V}/\dot{Q}$) mismatch or oxygen diffusion resistance (Rdiff)) results in a lateral displacement of the $FIO_2/SaO_2$ curve. Clearly, the lateral displacement of the $FIO_2/SaO_2$ curve (H-shift) is clinically a more significant problem as it describes a situation where large changes in oxygen saturation can occur for only small changes in $FIO_2$. In this situation the patient is at increased risk of an oxygenation problem.

The two parameter model of Sapsford et al. (1995), has been shown to fit data from normal subjects; patients before and after thoracotomy (Sapsford et al. 1995, de Gray et al., 1997); and patients during (Sapsford et al. 1995, Roe et al., 1997), and after (Roe et al., 1997) abdominal surgery. Similarly, the two-parameter model described by Andreassen et. al. has been shown to fit data from normal subject and postoperative cardiac patients (Andreassen, 1999) and a wide range of as yet un-published results. Examples of these results are shown in FIG. 3.

In contrary to detailed experimental approaches (e.g. the MIGET), these two parameter models can be used routinely in clinical practice. In particular, these techniques may find application in the monitoring and choice of therapeutic treatment for patients with left-sided heart failure, or to assess patients risk of post-operative hypoxaemia.

Until now, estimation of oxygenation parameters has involved manual titration of the $FIO_2/SaO_2$ curve and off-line estimation of the parameter values. This is time consuming with experimental times of approximately 45 minutes, not including the time required for off line parameter estimation. This limits the use of the method as a clinical tool.

DESCRIPTION OF THE INVENTION

It is an object of the present invention to provide a device for estimation of one or more respiratory parameters including oxygenation parameters and lung parameters relating to an individual in which the necessary quantities for enabling an estimation of respiratory parameters are collected automatically by a computer of the device so as to provide an automated estimation of said parameters.

It is a further object to provide a device wherein the necessary measurements at varying oxygen levels are obtained in an at least semi-automated manner whereby the experimental time for said estimation may be reduced. By reducing the procedural time these techniques have potential for routine clinical use.

It is a still further object to provide a device which is adapted for assessing a possible new target of the level of oxygen in the blood circulation based on the previously obtained measurement(s).

It is a yet still further object to provide a device, which is adapted for assessing an appropriate change in the current level of oxygen in the inspired gas to obtain a given target of the level of oxygen in the blood circulation.

The use of the device on humans is of particular interest, but the device may also be applied to farm animals such as pigs, or to domestic animals such as dogs.

The device might be of value in all kind of patients in which hypoxemia occurs or may occur. These conditions may e.g. be selected from the group comprising left sided heart failure, adult respiratory distress syndrome, pneumonia, postoperative hypoxemia, pulmonary fibrosis, toxic pulmonary lymphoedema, pulmonary embolisms, chronic obstructive pulmonary disease and cardiac shunting.

Thus, the present invention relates in a first aspect of the present invention to a device for determining one or more respiratory parameters relating to an individual, comprising a gas flow device having means for conducting a flow of inspiratory gas from an inlet opening to the respiratory system of the individual and a flow of expiratory gas from the respiratory system of the individual to an outlet opening, a gas-mixing unit for supplying a substantially homogeneous gas to the inlet opening of the gas flow device, first supply means for supplying a first gas to an inlet of the gas mixing unit and having first control means for controlling the flow of the first gas, second supply means for supplying a second gas having an oxygen fraction different to the gas supplied from the first supply means to an inlet of the gas mixing unit and having second control means for controlling the flow of the second gas, a computer for determining said one or more respiratory parameters, first detection means for detecting the level of oxygen ($SaO_2$, $SpO_2$, $PaO_2$, $PpO_2$) in the blood circulation of the individual and producing an output to the computer accordingly, and second detection means for detecting the level of oxygen ($FIO_2$, $FE'O_2$, $\overline{FE}O_2$, $PIO_2$, $PE'O_2$, $\overline{PE}O_2$) in the gas flow passing into or out of the respiratory system of the individual and producing an output to the computer accordingly, the computer being adapted for retrieving and storing at least two measurements being the concurrent output produced by the first detection means and the second detection means within a data structure, in which the two stored outputs are mutually related, in data storage means associated with the computer, the at least two measurements being conducted at respective levels of oxygen in the gas flow passing into the respiratory system, the computer further being adapted for determining at least one respiratory parameter (Rdiff, shunt, $\dot{V}/\dot{Q}$, H-shift, V-shift) being descriptive of the condition of the individual, the determination being based on the at least two measurements.

Hence, in its broadest aspect, the invention relates to a device for determining one or more respiratory parameters relating to an individual. By the term "individual" is herein understood an individual selected from the group comprising humans as well as farm animals, domestic animals, pet animals and animals used for experiments such as monkeys, rats, rabbits, etc.

By the term "respiratory parameters" is herein understood parameters relating to oxygen transport from the lungs to the blood, such as parameters related to abnormal ventilation, resistance to oxygen uptake from the lungs to the lung capillary blood, and parameters related to shunting of venous blood to the arterial blood stream. These respiratory parameters may be given as absolute values or relative values as compared to a set of standard values and the parameters may further be normalised or generalised to obtain parameters that are comparable to similar parameters measured for other individuals, at least for individuals of the same species.

Thus, the computer may further be adapted for determining at least two respiratory parameters (Rdiff, shunt, $\dot{V}/\dot{Q}$, H-shift, V-shift) being descriptive of the condition of the individual, and said parameter(s) (Rdiff, shunt, $\dot{V}/\dot{Q}$, H-shift, V-shift) may alternatively or additionally be generalised parameters being comparable to similar parameter(s) determined for other individuals.

In a preferred embodiment, the computer of the device is further adapted for performing a procedure at least once, the procedure comprising determining, based on at least two measurements, whether additional measurements are required, asserting a possible desired target defining a desired output of the first detection means, producing a possible control data item based on the target, and retrieving and storing, in the data structure, additional measurement results being the concurrent output produced by the first detection means and the second detection means. The control data item produced thereby may be outputted to a human operator by means of an output device so that the operator can adjust the level of oxygen in the inspired gas flow. Alternatively, the control data item may be used by another part of or a computer program within the computer or by an external control device for automatically control of the means for controlling the flow to the gas-mixing unit of at least one gas.

According to a preferred embodiment of the present invention, the second detection means are arranged for detecting the level ($FIO_2$, $PIO_2$) of oxygen in the gas flow passing into the respiratory system, and the device further comprises third detection means for detecting the level ($FE'O_2$, $F\overline{E}O_2$, $PE'O_2$, $P\overline{E}O_2$) of oxygen in the gas flow passing out of the respiratory system and producing an output to the computer accordingly, and fourth detection means for detecting variables (Vt, f, $\dot{V}$) of the gas flow passing the respiratory system and producing an output to the computer accordingly, said output being sufficient for the computer to establish the volume flow of gas passing the respiratory system, the computer being adapted for retrieving and storing output from the third detection means and the fourth detection means within the data structure relating these stored output mutually as well as with the output from the first detection means and the second detection means retrieved simultaneously. This/these measurement(s) enable(s) the computer to estimate or establish the oxygen consumption of the individual, either implicitly as part of the estimation of respiratory parameters, or the computer may further be adapted for explicitly establishing, based on said measurement(s), the oxygen consumption ($VO_2$) of the individual.

It is advantageous for the device according to the present invention that the computer is adapted to determine a parameter relating to an equilibrium state of the overall oxygen uptake or consumption of the individual based on the output of at least one of the detection means, to compare said parameter with a predefined threshold value and to produce a control data item accordingly if said parameter exceeds said threshold value. By determining whether an equilibrium state of the individual is obtained the timing of the steps of the procedure can be controlled efficiently and the overall time for performing the procedure may be further reduced.

It is also advantageous if the computer is adapted to asses the appropriate change in oxygen level in the inspired gas ($FIO_2$) from the current oxygen level ($FIO_2$) so as to achieve a given desired target oxygen level in the blood ($SaO_2$, $SpO_2$, $PaO_2$, $PpO_2$) and produce a control data item accordingly so that the oxygen level can be adjusted according to the data item. The actual adjustment may be performed by an operator of the device, in which case the data item is outputted to an output device. Alternatively and preferably the computer is adapted to operate the control means for controlling the flow to the gas mixing unit of at least one gas, in response to said control data item relating to the assessed change in oxygen level from the computer so as to change the oxygen level ($FIO_2$) in the inspired gas flow accordingly. The data item may instead be outputted to an external device, which is suitable for performing an automated control of the control means so as to adjust the oxygen level accordingly.

The assessment of change in oxygen level in the inspired gas may in an embodiment of the invention be based on a predefined set of data representing statistical distributions of variables stored within data storage means associated with the computer and on said measurements. Details of how this may be performed are disclosed in the detailed description of the invention. Alternatively, the assessment of change in oxygen level in the inspired gas may be based on the rate of change of the output of at least one of the detection means in response to a change in oxygen level ($FIO_2$) in the inspired gas flow. Typically, the oxygen level is changed stepwise or following a ramp function and the change over time of the oxygen level in the blood circulation or the level of oxygen in the expired gas is monitored. However, monitoring of another gas, such as $CO_2$, or another variable of the patient may additionally or alternatively be employed.

It is preferred that one gas is atmospheric air and that another of the gasses is more or less pure oxygen, i.e. has an oxygen fraction higher than that of atmospheric air, preferably in the range 0.85 to 1.00. Alternatively or additionally, another gas may be supplied which has an oxygen fraction below that of atmospheric air, i.e. in the range of 0.00 to 0.21, preferably of 0.00 to 0.05. Thereby the oxygen level of the inspired gas may be varied not only to level above that of atmospheric air but also below that level, thus providing a wide range of possible levels for performing measurements of the individual. The gas having a low oxygen fraction may be supplied from a source of more or less pure nitrogen $N_2$ or another suitable physiologically neutral gas, such as helium $H_2$, or it may be re-circulated expired gas from the individual, preferably after reduction of the level of $CO_2$ in the expired gas.

The device should ensure by means of a security arrangement that the oxygen saturation in the blood circulation of the individual is in the range of 65 to 100%, preferably for human beings in the range of 85 to 100% to avoid the risk of damage to organs. This condition varies for different species of animals.

The first detection means is preferably arranged for detecting a variable relating to the saturation level of oxygen in the arterial blood stream by means of an invasive or a non-invasive technique, which latter is preferred. Thus, the first detection means is in an advantageous embodiment a pulse oximeter. Alternatively, the level of oxygen in the venous blood stream may be measured by means of an invasive or a non-invasive technique, the latter again being the preferred one.

According to a second aspect, the present invention relates to a device for determining one or more respiratory parameters relating to an individual, comprising a gas flow device having means for conducting a flow of inspiratory gas from an inlet opening to the respiratory system of the individual and a flow of expiratory gas from the respiratory system of the individual to an outlet opening, a gas-mixing unit for supplying a substantially homogeneous gas to the inlet opening of the gas flow device, first supply means for supplying a first gas to an inlet of the gas mixing unit and having first control means for controlling the flow of the first gas, second supply means for supplying a second gas having an oxygen fraction different to the gas supplied from the first supply means to an inlet of the gas mixing unit and having second control means for controlling the flow of the second gas, a computer for determining said one or more respiratory parameters, first detection means for detecting the level of oxygen ($SaO_2$, $SpO_2$, $PaO_2$, $PpO_2$) in the blood circulation of the individual and producing an output to the computer accordingly, and second detection means for detecting the level of oxygen ($FIO_2$, $FE'O_2$, $F\overline{E}O_2$, $PIO_2$, $PE'O_2$, $P\overline{E}O_2$) in the gas flow passing into or out of the respiratory system of the individual and producing an output to the computer accordingly, the computer being adapted for retrieving and storing a first measurement being the concurrent output produced by the first detection means and the second detection means within a data structure, in which the two stored outputs are mutually related, in data storage means associated with the computer, the computer being further adapted for performing a procedure at least once, the procedure comprising determining, based on data stored within the data structure, whether additional measurements are required, asserting a possible desired target defining a desired output of the first detection means, producing a possible control data item based on the target, and retrieving and storing, in the data structure, additional measurement results being the concurrent output produced by the first detection means and the second detection means.

According to a third aspect, the present invention relates to a device for determining one or more respiratory parameters relating to an individual, comprising a gas flow device having means for conducting a flow of inspiratory gas from an inlet opening to the respiratory system of the individual and a flow of expiratory gas from the respiratory system of the individual to an outlet opening, a gas-mixing unit for supplying a substantially homogeneous gas to the inlet opening of the gas flow device, first supply means for supplying a first gas to an inlet of the gas mixing unit and having first control means for controlling the flow of the first gas, second supply means for supplying a second gas having an oxygen fraction different to the gas supplied from the first supply means to an inlet of the gas mixing unit and having second control means for controlling the flow of the second gas, a computer for determining said one or more respiratory parameters, first detection means for detecting the level of oxygen ($SaO_2$, $SpO_2$, $PaO_2$, $PpO_2$) in the blood circulation of the individual and producing an output to the computer accordingly, and second detection means for detecting the level of oxygen ($FIO_2$, $FE'O_2$, $F\overline{E}O_2$, $PIO_2$, $PE'O_2$, $P\overline{E}O_2$) in the gas flow passing into or out of the respiratory system of the individual and producing an output to the computer accordingly, the computer being adapted for retrieving and storing at least a first measurement being the concurrent output produced by the first detection means and the second detection means within a data structure, in which the two stored outputs are mutually related, in data storage means associated with the computer, the computer further being adapted to asses the appropriate change in oxygen level in the inspired gas ($FIO_2$) from the current oxygen level ($FIO_2$) so as to achieve a given desired target oxygen level in the blood ($SaO_2$, $SpO_2$, $PaO_2$, $PpO_2$) and produce a control data item accordingly.

The second aspect as well as the third aspect of the invention is disclosed above in the most fundamental embodiment which according to the present invention may be combined with the additional features disclosed above with relation to the first aspect of the invention.

The device may be used to obtain and/or compare one or more respiratory parameters relating to one or more individual(s). The individual may be a healthy individual, at risk of suffering from hypoxemia, or suffering from hypoxemia.

By the term "the individual is at risk of suffering from hypoxemia" is herein understood that the individual has a higher/increased risk of suffering from hypoxemia compared to a healthy individual. The increased risk of suffering from hypoxemia may e.g. be due to a hereditary predisposition, a post-operative condition and/or various diseases.

By the term "hypoxemia" is herein meant that the oxygen saturation in the blood from the individual is below 92%. Examples of diseases that can cause hypoxemia are left sided heart failure, adult respiratory distress syndrome, pneumonia, postoperative hypoxemia, pulmonary fibrosis, toxic pulmonary lymphoedema, pulmonary embolisms, chronic obstructive pulmonary disease and cardiac shunting.

The present invention also relates to a computer system comprising at least one general purpose computer having one or more computer programs stored within data storage means associated therewith, the computer system being arranged for as well as being adapted for determining one or more respiratory parameters according to the devices and/or methods disclosed above.

Furthermore, the present invention relates to a computer program product being adapted to enable a computer system comprising at least one general purpose computer having data storage means associated therewith and being arranged suitably to determine one or more respiratory parameters according to the devices and/or methods disclosed above.

| GLOSSARY | |
|---|---|
| FIO2 | Fraction of oxygen in inspired gas. |
| PIO2 | Pressure of oxygen in inspired gas. |
| SaO2 | Oxygen saturation of arterial blood, measured from a blood sample. |
| PaO2 | Pressure of oxygen in arterial blood, measured from a blood sample. |
| SpO2 | Oxygen saturation of arterial blood, measured transcutaneously. |
| PpO2 | Pressure of oxygen in arterial blood, measured transcutaneously. |
| FECO2 | Fraction of carbon dioxide in the mixed expired gas. |
| FE'O2 | Fraction of oxygen in expired gas at the end of expiration. |
| F$\overline{E}$O2 | Fraction of oxygen in the mixed expired gas. |
| P$\overline{E}$CO2 | Pressure of oxygen in the mixed expired gas. |
| PE'O2 | Pressure of oxygen in expired gas at the end of expiration. |
| Vt | Tidal volume, i.e. volume of gas breathed per breath. |
| f | Respiratory frequency, i.e. number of breaths per minute. |
| VO2 | Oxygen consumption, i.e. the amount of oxygen consumed by the tissues per minute. |
| Vd | Dead space i.e. the volume of the lung not involved in exchanging gases with the blood. |
| shunt | Respiratory parameter representing the faction of blood not involved in gas exchange. |
| Rdiff | Respiratory parameter representing a resistance to oxygen diffusion across the alveolar lung capillary membrane. |
| $\dot{V}$ | Ventilation. |
| $\dot{V}/\dot{Q}$ | Respiratory parameter representing the balance between ventilation and perfusion in a region of the lung. |
| V-shift | Respiratory parameter representing a vertical shift in plots of FIO2 against SaO2, FIO2 against SpO2, FE'O2 against SaO2, or FE'O2 against SpO2. |
| H-shift | Respiratory parameter representing a horizontal shift in plots of FIO2 against SaO2, FIO2 against SpO2, FE'O2 against SaO2, or FE'O2 against SpO2. |

has been estimated from a single parameter shunt model (Siggaard-Andersen and Siggaard-Andersen 1985), giving values of point A=15%, point B=15%, point C=20%, point D=25%.

Figure 1:
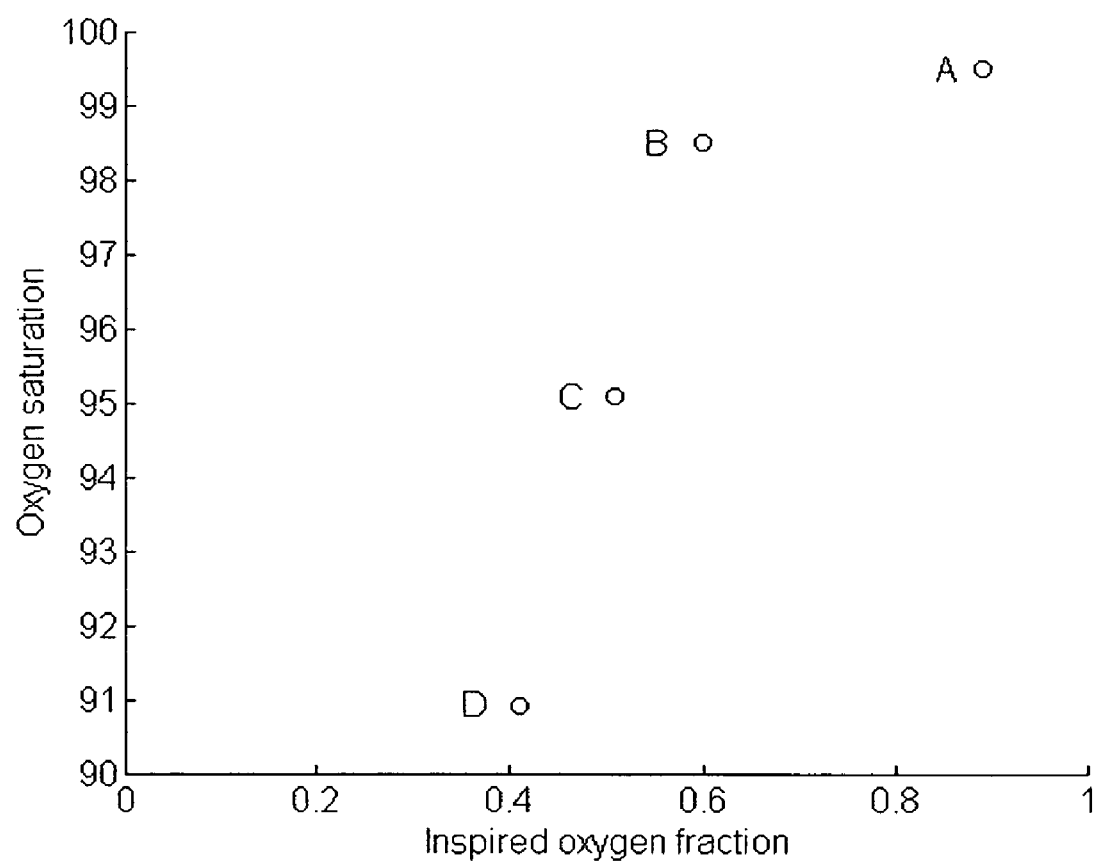
FIG. 1. Plot of the inspired oxygen fraction ($FIO_2$, x-axis) against the arterial oxygen saturation ($SaO_2$, $SpO_2$, y-axis) for 1 patient. For each data point (A–D) the "effective shunt"
Figure 2:
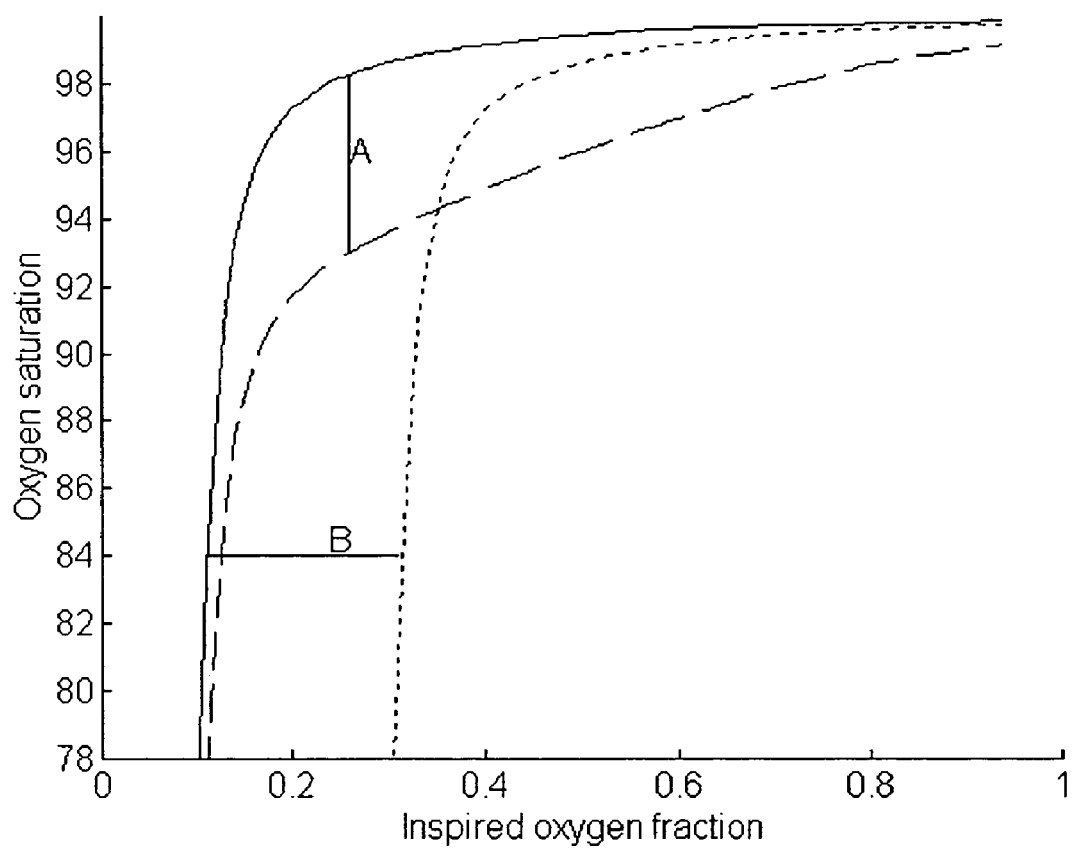

FIG. 2. Plots of the inspired oxygen fraction ($FIO_2$, x-axis) against model predicted arterial oxygen saturation ($SaO_2$, $SpO_2$, y-axis) for 1) a normal subject with shunt=5% and Rdiff=0 kPa/l/min) (solid line), 2) a hypothetical patient with a Rdiff or ventilation/perfusion disorder (dotted line), and 3) a hypothetical patient with a shunt disorder (dashed line).

Line A illustrates the vertical displacement of the curve (V-shift) due to a shunt disorder, whilst line B illustrates the horizontal displacement of the curve (H-shift) due to a ventilation perfusion of oxygen diffusion abnormality.

Figure 3:
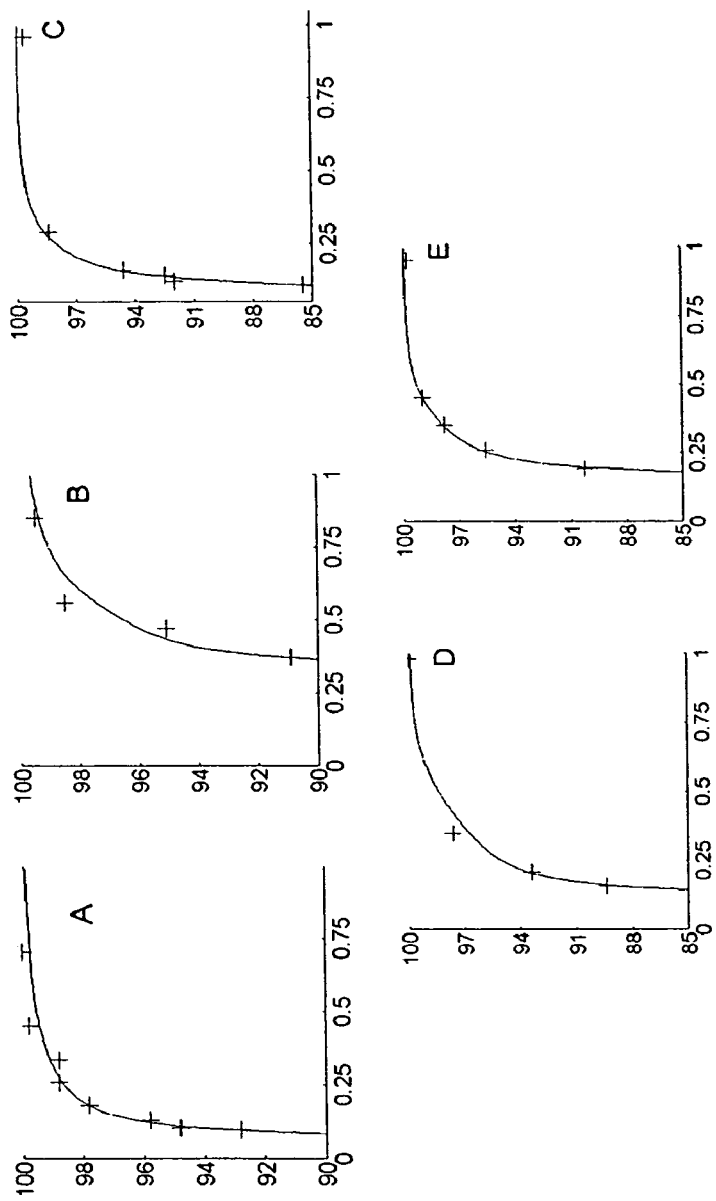

FIG. 3. Plots of the inspired oxygen fraction ($FIO_2$, x-axis) against arterial oxygen saturation ($SaO_2$, $SpO_2$, y-axis). Each of the vignettes illustrates data (crosses) and model predicted curves fitted, to this data from: A—a normal subject (shunt=5%, Rdiff=−1.5 kPa/(l/min)), B—a post-operative cardiac patient (shunt=9.5%, Rdiff=81.0 kPa/(l/min)), C—a post-operative hysterectomy patient (shunt=7%, Rdiff=15.2 kPa/(l/min)), D—a poorly compensated cardiac patient (shunt=15%, Rdiff=22.9 kPa/(l/min)), and E—a patient residing in the intensive care unit (shunt=7%, Rdiff=31.0 kPa/(l/min)).

Figure 4:
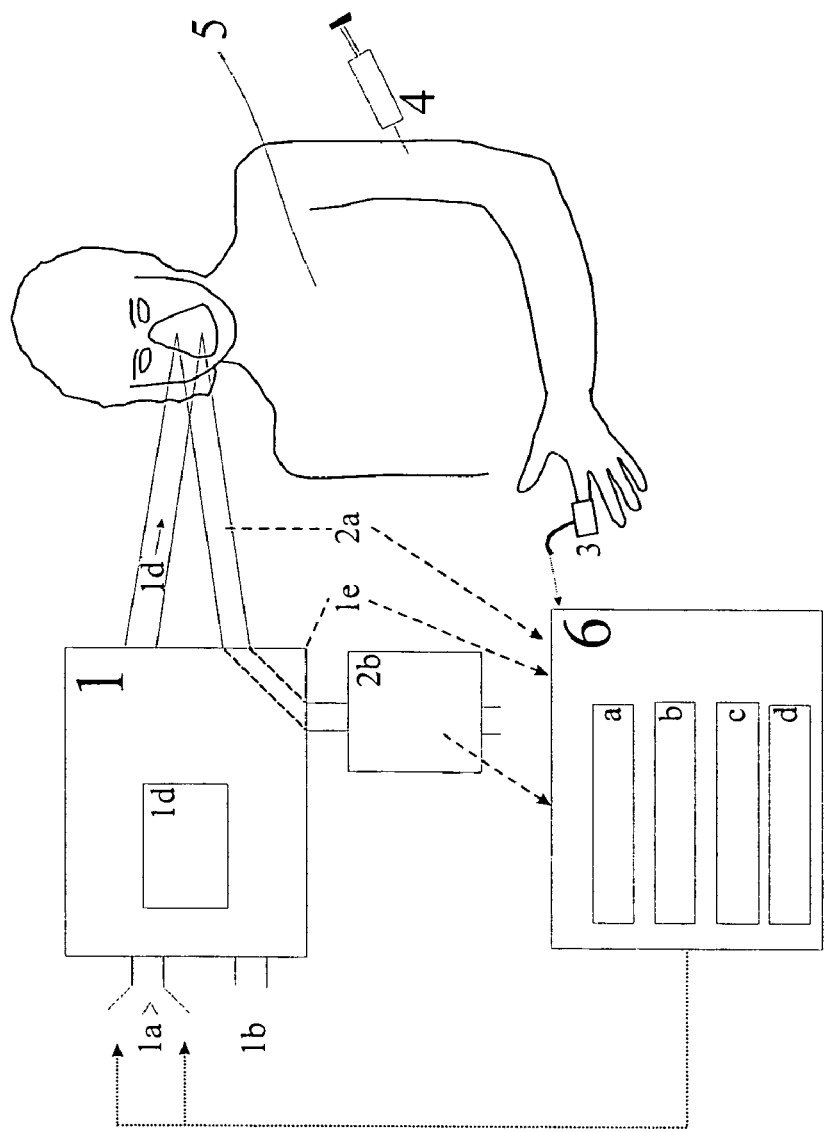

FIG. 4. Experimental set-up working with nitrogen for subathmospheric oxygen levels. The system includes: 1) A Gas Delivery Unit including gas inlets (1a, 1b), a gas mixer (1c), a flow or pressure gradient (1d), and equipment for the measurement and/or setting of inspired oxygen fraction ($FIO_2$), tidal volume and respiratory frequency (1e); $_2$) Equipment for measurement of expired gases including an oxygen monitor placed so as to measure end tidal oxygen fraction (2a), and/or an expiratory reservoir, used with an oxygen monitor and/or a carbon dioxide monitor to measure the fraction of gas in or leaving the expiratory reservoir (F $EO_2$, $FECO_2$) (2b); 3) Measurement of arterial oxygen saturation ($SaO_2$) via e.g. a pulse oxymeter ($SpO_2$); 4) Measurements of arterial or venous blood gas samples (optional); 5) Measurement of cardiac output (optional); 6) A computer system including software for automatic collection of data (6a), monitoring the steady state of the patients/subjects oxygenation (6b), a feedback controller for adjusting inspired oxygen fraction (6c), and estimation of gas exchange parameters. Dashed arrowed lines illustrate the flow of information to the computer. Dotted arrowed lines illustrated the control of the gas delivery unit by the computer.

Figure 5:
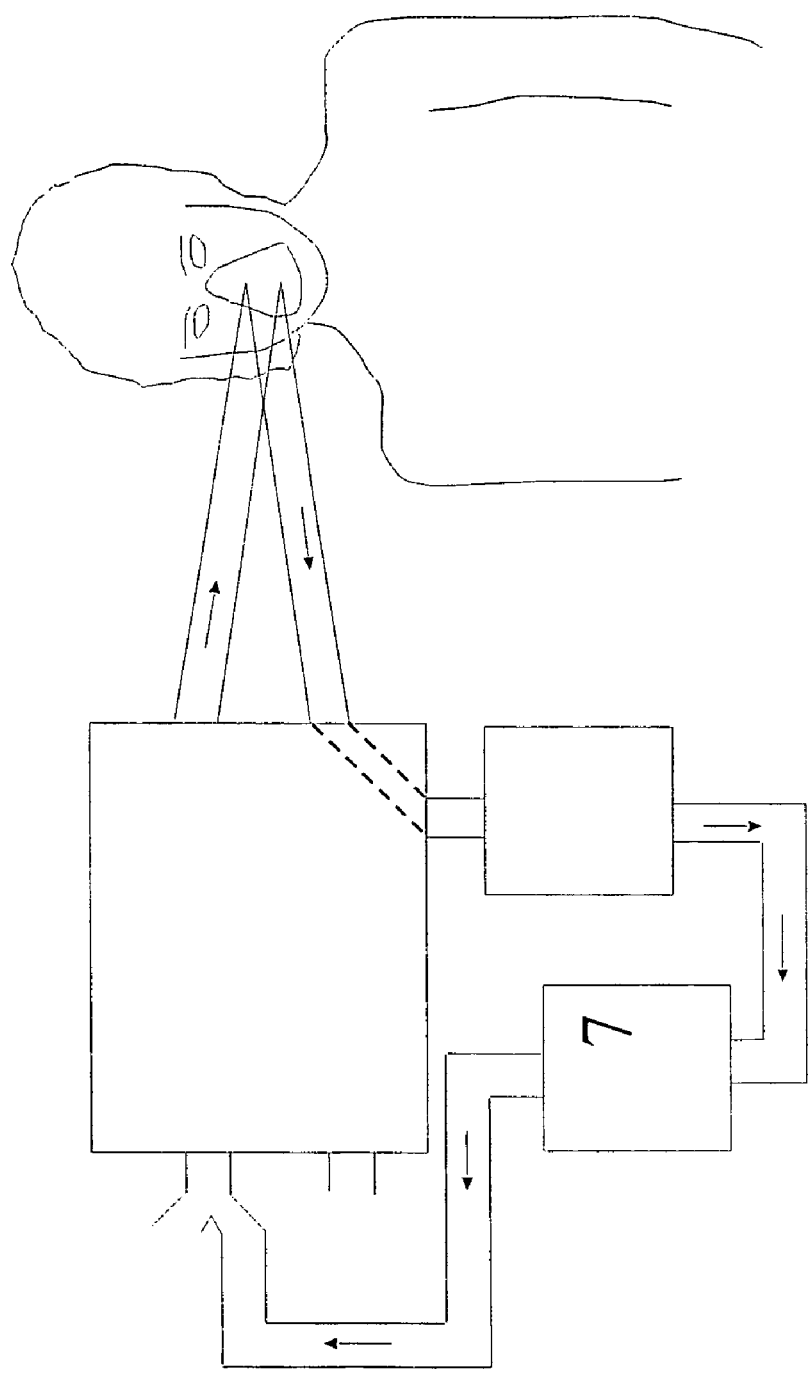

FIG. 5. Experimental set up using a rebreathing technique for subatmospheric oxygen levels. FIG. 5 illustrates a modification to the set-up of FIG. 4. It includes all other components illustrated in FIG. 4, plus a carbon dioxide removal device to eliminate carbon dioxide from the re-inspired gases (box 7). All other points 1–6 are the same as FIG. 4.

Figure 6:
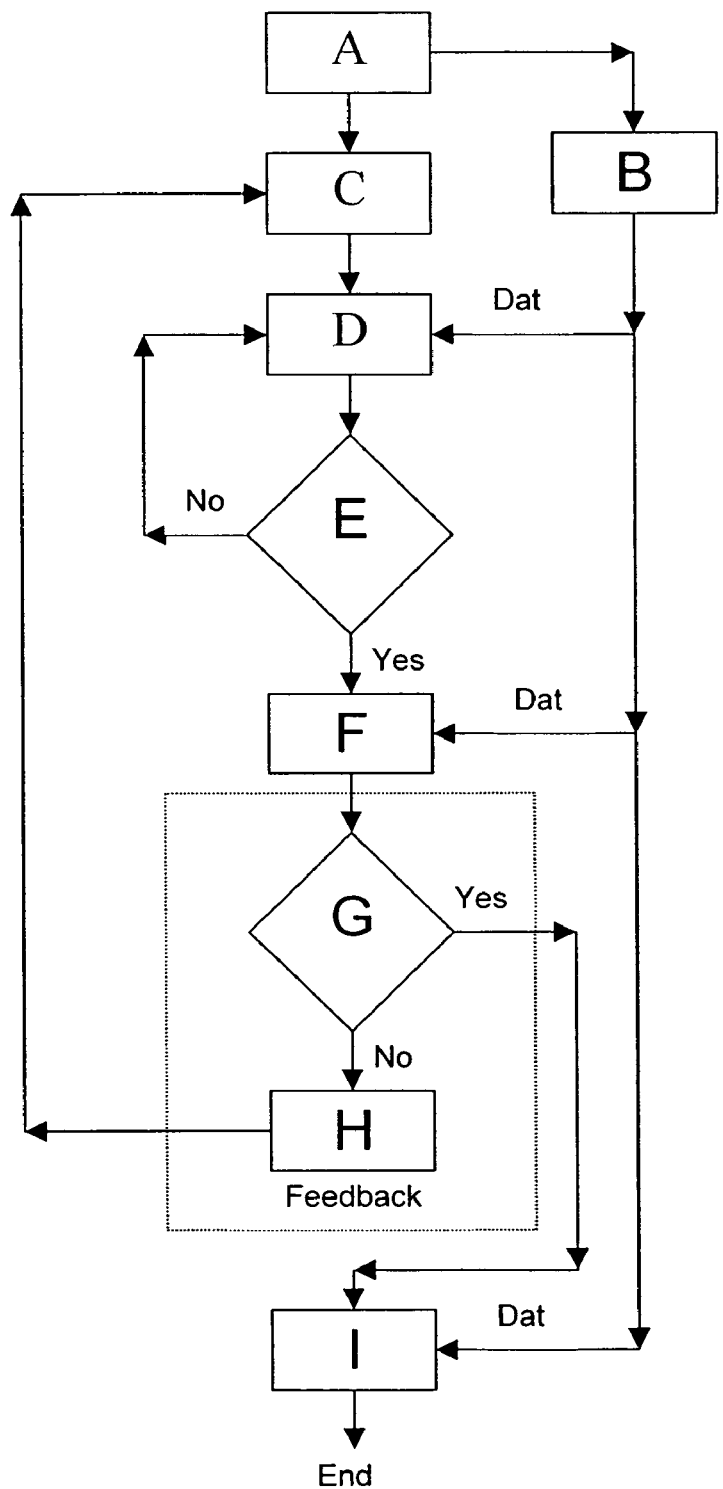

FIG. 6. Flow chart for a measurement of variables for determination of lung parameters.
A: Begin parameter estimation if $FIO_2$>1.00 and $SpO_2$>0.85
B: Continuous data recording from gas delivery unit, pulse oxymeter and expiratory gas measurement devices.
C: Set oxygen level ($FIO_2$).
D: Monitor $O_2$ equilibrium.
E: Equilibrium level.
F: Record measurement.
G: Sufficient number of measurements?
H: Estimate new $FIO_2$.
I: Estimate Pulmonary Parameters.

Figure 7:
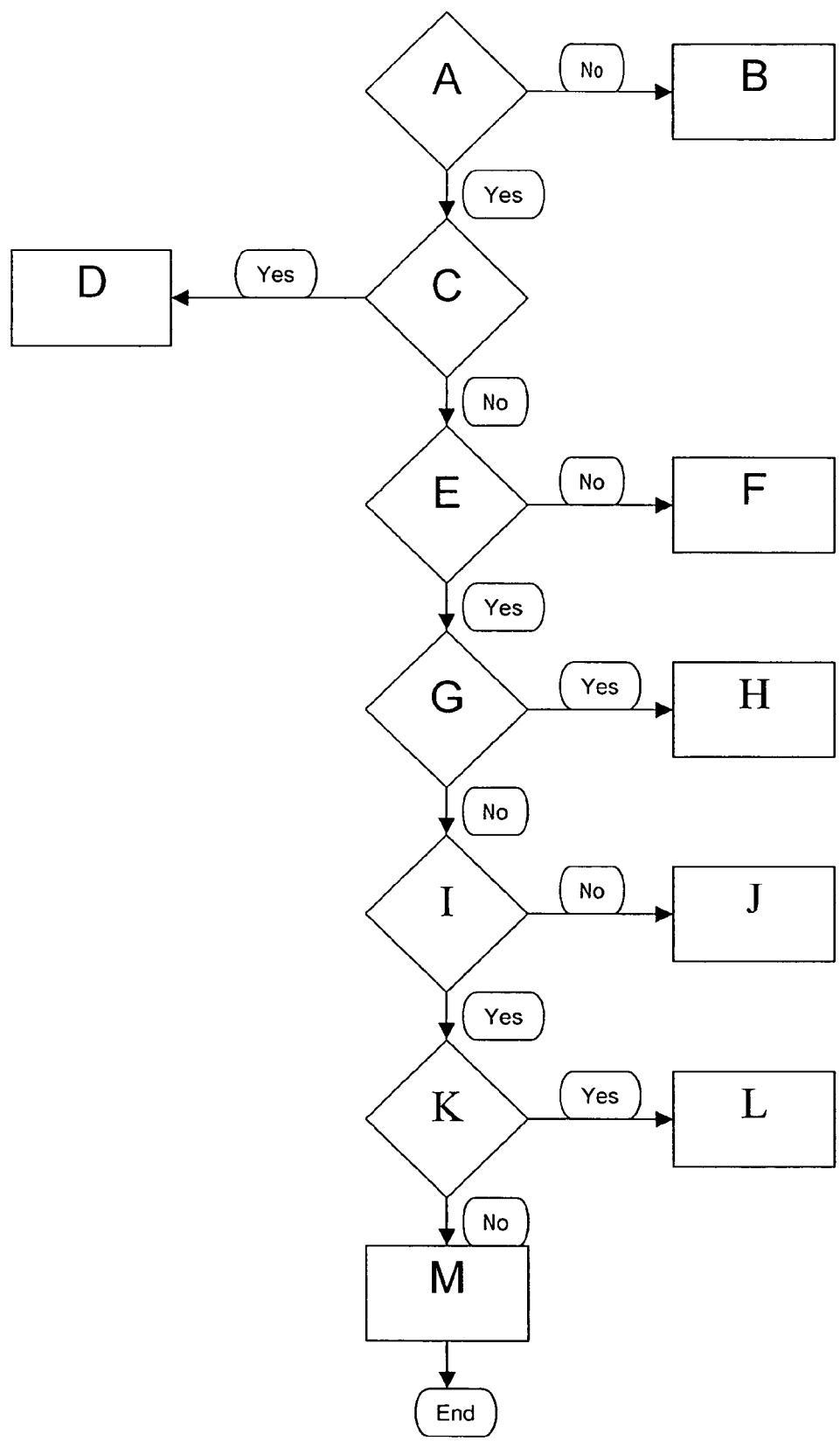

FIG. 7. (algorithm 1) Assessing whether another measurement is necessary and determining the target $SpO_2$ for that measurement. If current $FIO_2$=1.00 and $SpO_2$<0.85% do not perform measurement.
A: Is there 1 measurement of ($SpO_2$) 1 where $0.85 \leq (SpO_2)$ 1<0.92?
B: Target $SpO_2$: $0.85 \leq (SpO_2)$ 1<0.92
C: Was $FIO_2$=1.00 at this measurement?
D: Patient too sick for measurement.
E: Is there 1 measurement of ($SpO_2$) 2 where $0.92 \leq (SpO_2)$ 2<0.95?
F: Target $SpO_2$: $0.92 \leq (SpO_2)$ 2 <0.95
G: $FIO_2$=1.00 at this measurement?
H: Target $SpO_2$: ($SpO_2$) $1 \leq SpO_2 < (SpO_2)$ 2
I: Is there 1 measurement of ($SpO_2$) 3 where $0.95 \leq (SpO_2)$ 3<0.98?
J: Target $SpO_2$: $0.95 \leq (SpO_2)$ 3<0.98
K: Was $FIO_2$=1.00 at this measurement?
L: Target $SpO_2$: ($SpO_2$) $2 \leq SpO_2 < (SpO_2)$ 3
M: Set $FIO_2$=1.00.

Figure 8:
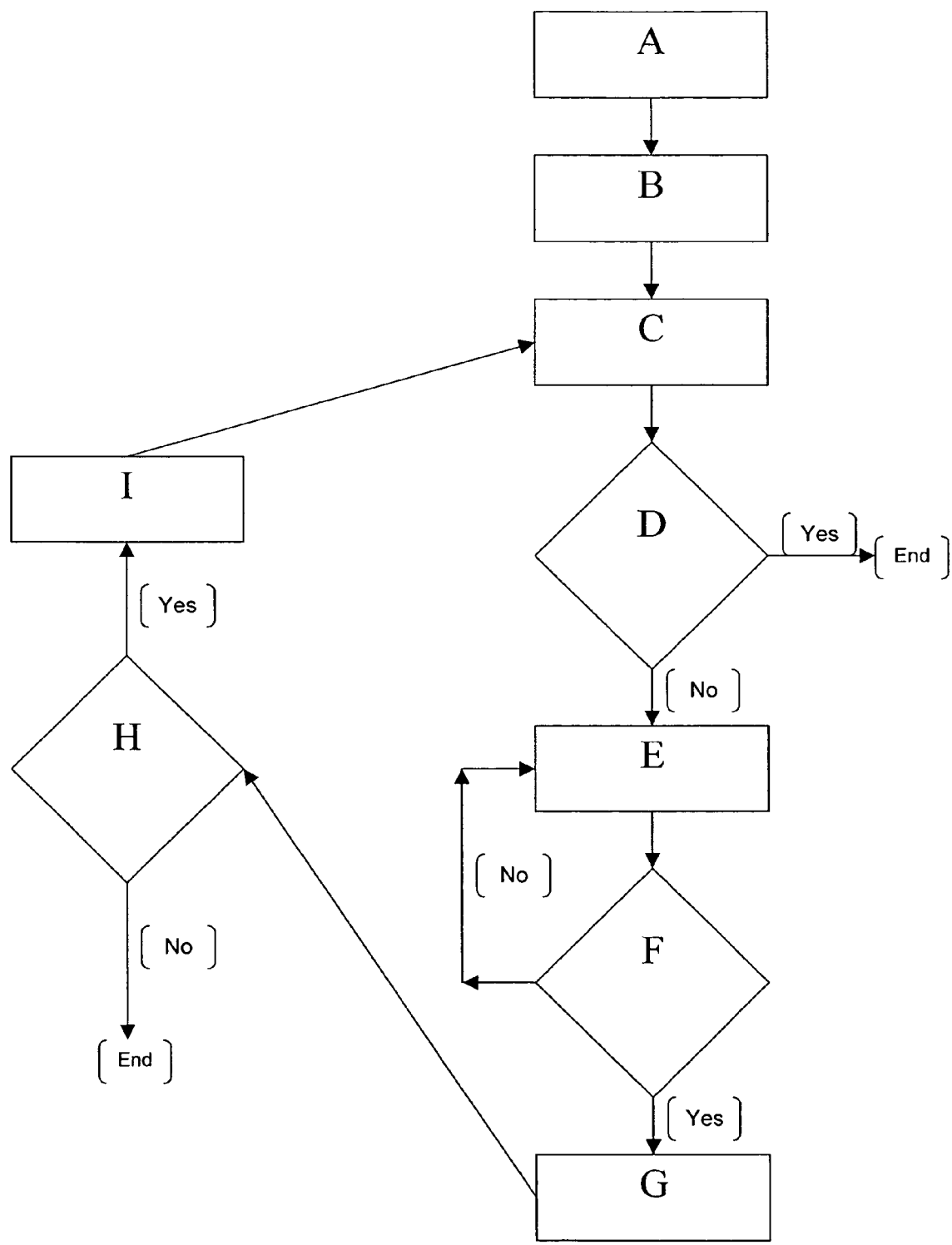

FIG. 8 (algorithm 2) This controller uses a mathematical model of oxygen transport with two parameters, shunt and either diffusion resistance or $\dot{V}/\dot{Q}$ mismatch. Parameters are implemented as stochastic variables and as such have a probabilistic distribution.

A: Select Appropriate a Priori Estimates for Parameters
The patients lung parameters are represented as stochastic variables with probability distributions. These parameters need to be initialised with a priori distributions. If the patients lung parameters have been investigated previously, or if the patient belongs to a well-defined population there may be well-defined a priori distributions for the patient's lung parameters.

B: Target $SpO_2$=First Target Level

C: Update Parameter Estimates with Measurement Data.
This is a Bayesian update of the parameter estimates for the measured values. The output of this process being revised probability distributions for the patients' lung parameters.

D: Is the Parameter Probability Mass Distributed within Range.
If the probability distributions for the patients' lung parameters have a very narrow distribution, then they are estimated with good precision, and no further $FIO_2$ settings or measurements are required.

E: Predict $SpO_2$ (distribution) when $FIO_2$ lowered/raised by a predetermined percentage, using parameter estimates. The predetermined percentage is dependent on the conditions and the patient. The mathematical models can be used to predict the effects of varying $FIO_2$ giving the current estimate of the probability distributions for the patients' lung parameters. Predictions can be obtained in terms of the probability of a certain oxygen saturation of the blood.

F: Is 10% of Probability Mass <Target $SpO_2$.
If the predicted probability distribution for $SpO_2$ is distributed evenly about the target $SpO_2$ then the $FIO_2$ is selected for the next measurement.

G: Set the Selected $FIO_2$ Level.

H: Continue the Algorithm only if there are more Target $SpO_2$ Levels?

I: Set the next Target $SpO_2$ Level.

Figure 9:
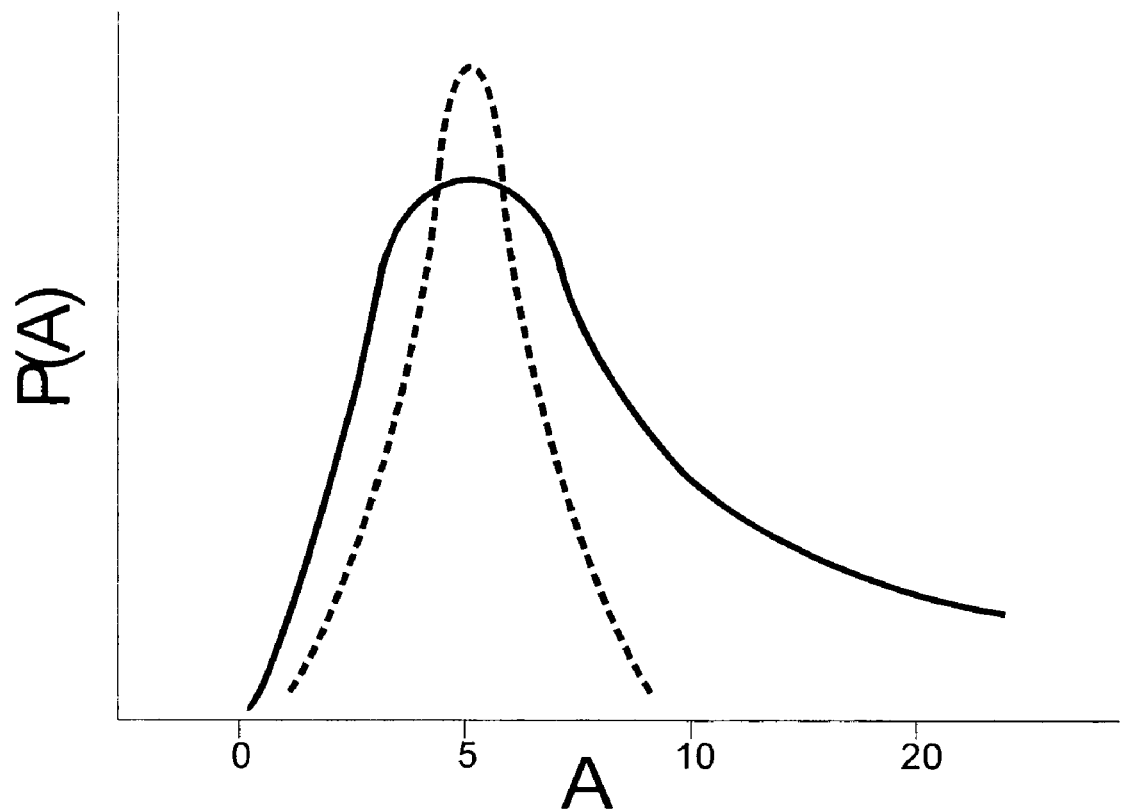

FIG. 9 illustrates a graph of a patients parameter (A, x-axis) plotted against the probability that this parameter takes a certain value (P(A), y-axis). One of these graphs is used for each patient parameter (i.e. shunt, Rdiff and or $\dot{V}/\dot{Q}$). Before a measurement procedure begins an a priori distribution is obtained for each of the patient parameters from computer storage. Subsequently, these a priori estimates are updated as measured data presents. Typical distributions of the shunt parameter are illustrated for a normal healthy subject both a priori (solid line, mean shunt=5%), and following update of the distribution with measured data (dashed line).

Figure 10:
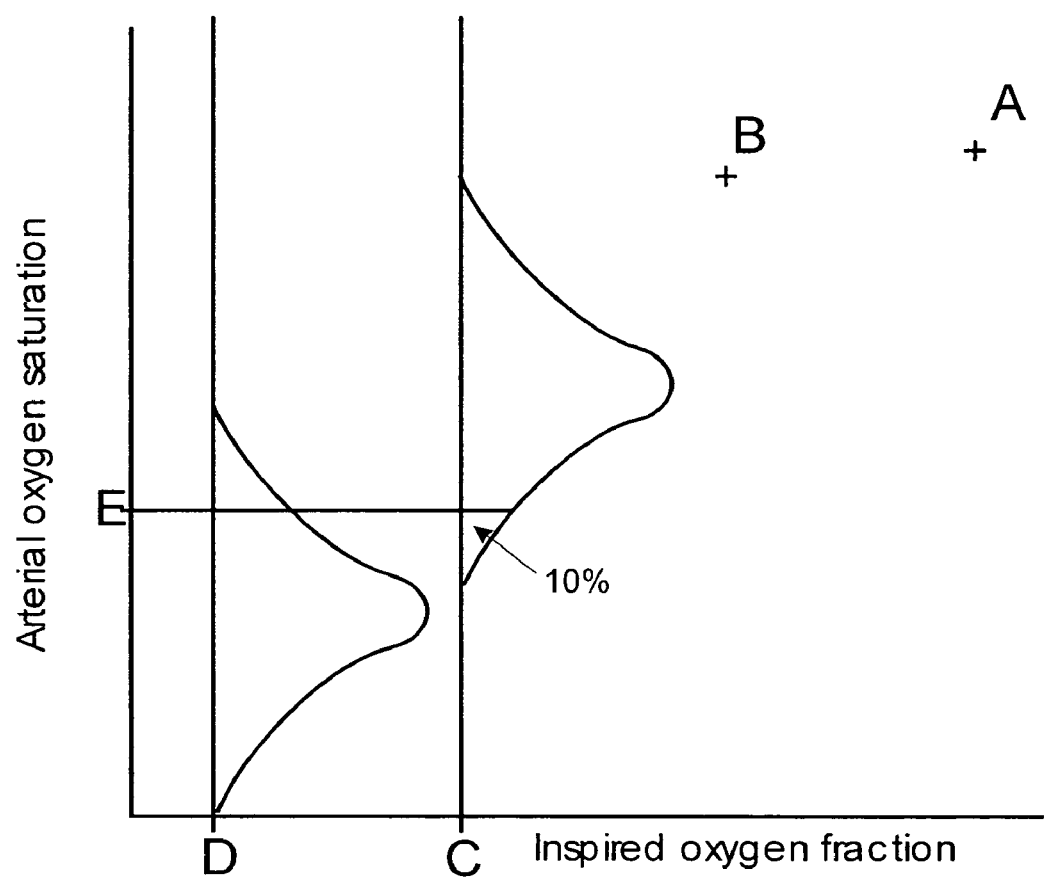

FIG. 10 illustrates model predicted arterial oxygen saturation ($SaO_2$, $SpO_2$, y-axis) when varying inspired oxygen fraction ($FIO_2$, x-axis). Points A and B are measured $FIO_2$/$SpO_2$ values which are used to update parameter values (i.e. P(parameters|measurements)). The updated parameter values are then used to predict the change in $SpO_2$ on varying $FIO_2$ (i.e. $P(SpO_2|FIO_2)$). These predictions are illustrated for two different $FIO_2$ levels (C and D) and are plotted as probability distributions. The appropriate $FIO_2$ level is then selected so that $\leq x\%$ (in this case 10%) of the probability distribution is below the target $SpO_2$ level (E).

DETAILED DESCRIPTION OF THE INVENTION

The following description of preferred embodiments of the invention will focus on a device for automating the estimation of lung parameters. This device (Automatic Lung Parameter Estimator=ALPE) enables reduction in the time taken to obtain estimates of oxygenation parameters, with the total time including on-line estimation of parameters taking 10–15 minutes. By reducing the procedural time these techniques have potential for routine clinical use. This is only possible because of the substantial novelty in the ALPE which may include functionality for:

1) On-line continuous data collection
2) Automatic assessment of the timing of measurements
3) Automatic assessment of the next target $SpO_2$
4) Automatic assessment of the appropriate $FIO_2$ settings to achieve the target $SpO_2$
5) Automatic control of the $FIO_2$
6) On-line parameter estimation
7) Automatic assessment of the number of measurements required This functionality is achieved through a novel apparatus including ventilatory equipment, blood gas analysis equipment and computer hardware and software as described below.

Description of the Automatic Lung Parameter Estimator (ALPE):

The Automatic Lung Parameter Estimator (ALPE) illustrated in FIG. 4 may be used to assess oxygenation parameters in any patient, with these parameters being useful for diagnostic or monitoring purposes. Monitoring of patients' lung parameters is of particular value for those patients with ongoing treatment for example those patients artificially ventilated or those receiving therapies for left-sided heart failure.

The ALPE can automatically determine the parameters of models of oxygen transport. These parameters are obtained from numerous measurements including the $FIO_2$/$SpO_2$ curve, with this curve being constructed automatically by the apparatus for $SpO_2$ varying between 0.85 to 1.00.

ALPE illustrated in FIG. 4 includes the following (numbers before paragraphs refer to the numbers in FIG. 4):

1) A Gas Delivery Unit—This equipment includes: Two or more gas inlets, shown here delivering a) oxygen or nitrogen, and b) air; c) A gas mixer capable of mixing two input gases to the required fraction or concentration; d) A means of delivering the gases to the patient/subject i.e. a flow or pressure gradient; e) Equipment for the measurement and/or setting of inspired oxygen fraction ($FIO_2$), tidal volume and respiratory frequency (or minute volume). The gas delivery unit included in the system can either be a stand-alone device offering only this functionality, or any other device, which includes this functionality such as patient ventilation devices (respirators) commonly used for intensive care patients. Ventilatory gases are delivered to and removed from the patient/subject through a face mask, mouth piece combined with a nose clip, laryngeal endotracheal tube etc.

2) Measurement of expired gases—Expired gases are measured using either: a) An oxygen monitor, placed so as to measure expiratory gases and sensitive enough to give measurement of the end tidal oxygen fraction ($FE'O_2$), i.e. the fraction of oxygen in the expired gases at the end of an expiration. b) An expiratory reservoir, placed so as to capture expiratory gases during the course of the expiration, used in combination with an oxygen monitor and/or a carbon dioxide monitor sensitive enough to measure the fraction of gas in or leaving the expiratory reservoir ($F\overline{E}O_2$, $F\overline{E}CO_2$).

3) Measurement of arterial oxygen saturation ($SaO_2$) via e.g. a pulse oxymeter ($SpO_2$).

4) Measurements of arterial or venous blood gas samples may be taken or may be monitored continuously by invasive means and put manually into the system. These measurements are optional.

5) Measurement of cardiac output may be put manually into the system. This measurement is optional.

6) A computer system including software for
   a) Automatic collection of data from the gas delivery unit ($FIO_2$, Vt, f), the expired gas measurement devices ($FE'O_2$, $F\overline{E}O_2$, $F\overline{E}CO_2$ (optional)), and the pulse oxymeter (or any other measure of $SpO_2$ or $SaO_2$).
   b) Monitoring the steady state of the patients/subjects oxygenation.
   c) A feedback controller, which determines whether a further measurement is required and automatically adjusts the inspired oxygen fraction to the most appropriate level.
   d) Estimation of gas exchange parameters from the data collected.

Dashed arrowed lines on FIG. 4 illustrate the flow of information to the computer. Dotted arrowed lines illustrated the control of the gas delivery unit by the computer.

A modification to the system is also included as part of this patent (FIG. 5). For environments where nitrogen ($N_2$) or another physiologically neutral gas is not available the oxygen content of inspired gases can be reduced lower than air ($FIO_{2air}$=21%) by re-breathing expired gases. In this situation, in addition to all other components illustrated in FIG. 4 a carbon dioxide removal device is included in the system to eliminate carbon dioxide from the re-inspired gases (box 7 FIG. 5). All other points 1–6 described above are the same as FIG. 4.

DETAILED DESCRIPTION OF THE FLOWCHARTS

The flowcharts are provided solely to illustrate the invention by reference to specific embodiments. These flowcharts and the algorithms included herein, while illustrating certain aspects of the invention, do not portray the limitations or circumscribe the scope of the disclosed invention.

FIG. 6 is a flowchart illustrating the processes involved during operation of the ALPE.

Box A: After set-up of the equipment as illustrated in FIGS. 4 and 5 the parameter estimation procedure begins.

Box B: As part of this process the computer continuously collects data from the other equipment, including $FIO_2$ and $SpO_2$ (and/or $FE'O_2$, Vt, f, $\overline{FEO}_2$, $\overline{FECO}_2$).

Box C: An initial inspired oxygen fraction is selected ($FIO_2$) and delivered to the patient. This is done automatically via the computer or manually by the doctor. Initially $FIO_2$ is usually that of air (21%) but any other value of $FIO_2$ can be used as the starting point for the experiment. At all times the patient/subject is required to have an arterial oxygen saturation ($SpO_2$) greater than or equal to 0.85. The initial $FIO_2$ may therefore be set to a high level so as to achieve $SpO_2 \geq 0.85$.

After setting the inspired oxygen level the patients' oxygen system will take time to equilibrate. This usually occurs within 2–5 minutes after the perturbation. The equilibrium of the patients oxygen system is monitored automatically by the "steady state monitor" software in the computer. This functionality substantially reduces the time taken to perform a parameter estimation and is only possible because of the apparatus.

Box D: The assessment of equilibrium can be performed using a number of algorithms, e.g. as follows:
1) The arterial oxygen saturation ($SpO_2$) remains constant within a predefined range over a predefined time period.
2) The difference between the fraction of oxygen in the inspired and expired gas remains constant within a predefined interval over a predefined time period.
3) The calculated oxygen consumption ($VO_2$) remains constant within a predefined interval for a predefined time period.

The oxygen consumption ($VO_2$) is calculated automatically by the computer from the continuously monitored variables using the equation $VO_2 = f(Vt-Vd)$ ($FIO_2 - FE'O_2$) assuming or calculating a value of Vd, or using $VO_2 = fVt$ ($FIO_2 - \overline{FEO}_2$), or any variation in this equation where a combination of measurements of end tidal or mixed expired gases are used to estimate the oxygen consumption.

Box E: When equilibrium is achieved a measurement is recorded (Box F).

Box F: This measurement includes the current values of all continuously monitored variables as described previously. It can also include measurements of blood gases in from and arterial or venous blood and a cardiac output measure obtained from equipment e.g. a pulmonary catheter. The last measurements are optional.

Box G: Following a measurement it is decided either automatically by the apparatus or manually by the clinician whether a sufficient number of measurements have been performed, or whether to change the inspired oxygen fraction to a new level and take a further measurement when equilibrium is achieved.

Box H: It is also decided either automatically by the apparatus or manually by the clinician what level of $FIO_2$ should be selected for a new measurement (if necessary). An experiment consists of not less than 2 measurements at varying $FIO_2$ levels, with $SpO_2$ in the range 0.85–1.00. It is important that the setting of $FIO_2$ levels achieve data points with $SpO_2$ well distributed between 0.85–1.00.

Examples of algorithms, which can be used to implement Box G and Box H are included in the next section.

Box I: After an adequate set of measurements has been taken parameters are estimated which describe the patients lung function. Parameter estimation is performed automatically using one or more of the following algorithms:
1) Graphical estimation of displacement(s) of the $FIO_2/SpO_2$ curve or the $\overline{FEO}_2/SpO_2$ curve.

Values of inspired or expired oxygen fraction can be plotted against the arterial oxygen saturation ($SpO_2$) and graphical methods used to measure the horizontal (H-shift) and vertical displacement (V-shift) of the data (or interpolated data) from a normal reference range as illustrated in FIG. 2.
2) Estimation of the parameters of models of oxygen transport.

All data collected for each of the measurements can be used with mathematical models of oxygen transport to estimate parameters describing oxygenation. Parameters can e.g. be estimated describing the shunting of pulmonary blood (shunt) and either a resistance to oxygen diffusion or a mismatch between the ventilation and perfusion of the lung.

Algorithms for Automating boxes G and H in FIG. 6:

Numerous algorithms can be devised which enable assessment of:
a) Whether a new measurement is required.
b) What is the target $SpO_2$ for this measurement.
c) What inspired oxygen fraction ($FIO_2$) setting should be used to obtain the target $SpO_2$ These algorithms include those with complete computer automation of points a–c, and where points a–c are assessed using clinical judgement.

Two examples of these algorithms are presented here. The first includes points a and b. The second includes points a and c, using mathematical models of oxygen transport to asses the appropriate $FIO_2$ setting.

It should be noted that these algorithms are only illustrations of the control system of ALPE and that any other algorithms which can be used to assess points a, b and c are included in the patent application.

Algorithm 1: This algorithm covers points a and b above, and is illustrated in a flowchart (FIG. 7). It should be noted that if the current $FIO_2=1.0$ and the current $SpO_2$ is <0.85, then the patient is too ill to perform a lung assessment.

Algorithm 2: This algorithm covers points a and c i.e. it assesses whether a measurement is required and estimates the appropriate $FIO_2$ setting for the next measurement given a target $SpO_2$. The algorithm is illustrated in the flowchart FIG. 8. This algorithm uses a mathematical model of oxygen transport with two parameters. Parameters are implemented as stochastic variables and as such have probability distributions as illustrated in FIG. 9.

In box A (FIG. 9) the appropriate a priori estimates are obtained for the parameter distributions. If the patients lung parameters have been investigated previously, or if the patient belongs to a well-defined population there may be well defined a priori distributions for the patient's lung parameters. Alternatively, default parameter settings can be used. An example illustrating probability distributions on a parameter e.g. "shunt" or diffusion resistance "Rdiff" is illustrated in FIG. 9.

In box B the predefined target $SpO_2$ level is retrieved from computer storage.

In box C the parameters' probability distributions are updated with the measured data.

This is a Bayesian update of the parameter estimates for the measured values, such that the probability of the parameter values given the measurements (P(parameters|measurements)) can be calculated from Bayes theorem i.e.

$$P(\text{parameters} | \text{measurements}) = \frac{P(\text{measurements} | \text{parameters}) P(\text{parameters})}{P(\text{measurements})}$$

The output of this process being revised probability distributions for the patients' lung parameters updated to reflect the new information obtained from the measurements. These probability distributions are usually somewhat narrower than the a priori estimates as illustrated in FIG. 9.

Box D decides whether a further measurement is required. If the updated probability distributions for the patients' lung parameters have a very narrow distribution, then they are estimated with good precision, and no further $FIO_2$ settings or measurements are required. If a further measurement is required then it is necessary to find the appropriate $FIO_2$ setting so as to reach the next target $SpO_2$. This is done in several steps: first the mathematical models are used to predict $SpO_2$ when the $FIO_2$ level is lowered or raised by a predetermined percentage. The predetermined percentage is dependent on the conditions and the patient. $SpO_2$ is then predicted using the updated parameter estimates and the equation:

$$P(SpO2 | (FIO2)) = \sum_{param} P(SpO2 | FIO2, \text{parameters}) P(\text{parameters})$$

where P(parameters) is the current joint probability of all the parameter estimates. The output from this procedure is a set of probability distributions about $SpO_2$ on varying $FIO_2$ values, as illustrated in FIG. 10. Next (box F), an $FIO_2$ level is selected. The $FIO_2$ level is chosen such that a small fraction (e.g. 10%) of the predicted probability mass is below the target $SpO_2$ (see FIG. 10). Selecting an $FIO_2$ where only a small fraction of the predicted $SpO_2$ probability mass is below the target is a safety feature of this algorithm. Effectively, it means that it is unlikely that the patients $SpO_2$ will fall below the target value on modification of $FIO_2$. After setting the new $FIO_2$ level the $SpO_2$ target is modified and the above procedure repeated.

REFERENCES

Andreassen, S., Egeberg, J., Schröter, M. P., Andersen, P. T., (1996) Estimation of pulmonary diffusion resistance and shunt in an oxygen status model. Comput Methods Programs Biomed, vol 51, pp 95–105.

Andreassen, S., Rees, S. E., Kjaergaard, S., Thorgaard, P., Winter, S. M., Morgan, C. J., Alstrup, P., and Toft, E. (1999). Hypoxemia after coronary bypass surgery modeled by resistance to oxygen diffusion. Critical Care Medicine, vol 27, pp 2445–2453.

de Gray, L., Rush, E. M., Jones, J. G., (1997). A non-invasive method for evaluating the effect of thoracotomy on shunt and ventilation perfusion inequality. Anaesthesia, vol. 52, pp 630–635.

King, T. K. C, Weber, B., Okinaka, A., Friedman, S. A., Smith, J. P., Briscoe, W. A. (1974). Oxygen transfer in catastrophic respiratory failure. Chest, vol. 65, pp 40S–44S.

Rees, S. E., Rutledge G. W., Andersen P. T., Andreassen, S. (1997). Are alveolar block and ventilation-perfusion mismatch distinguishable in routine clinical data. In: Proceedings of the European society of computers in anaesthesia and intensive care conference, Erlangen, Germany, Sep. 18–19, 1997.

Riley, R. L., Counard A. (1951a) Analysis of factors affecting partial pressure of oxygen and carbon dioxide in gas and blood of the lungs: Theory. J Applied Physiol., vol 4, pp 77–101.

Riley, R. L., Counard A., Donald, K. W. (1951b). Analysis of factors affecting partial pressure of oxygen and carbon dioxide in gas and blood of the lungs: Method. J. Applied Physiol., vol 4, pp 102–120.

Roe P. G., Galdeirab, R., Sapsford., Jones, J. G. (1997). Intra-operative gas exchange and post-operative hypoxaemia. European Journal of Anaesthesiology, vol 14, pp 203–210.

Sapsford, D. J., Jones J. G. (1995). The PiO2 vs. $SpO_2$ diagram: a non-invasive measure of pulmonary oxygen exchange. European Journal of Anaesthesiology, vol 12, pp 369–374.

Siggaard-Andersen M, Siggaard-Andersen 0 (1995). Oxygen status algorithm, version 3, with some applications, Acta Anaesthesiol Scand. Vol. 39, Supp. 107, pp 13–20.

Wagner, P. D., Saltzman, H. A., West, J. B. (1974). Measurement of continuous distributions of ventilation-perfusion ratios: theory. J. Appl. Physiol. Vol 36(5): 588–599.

Wagner, P. D., Hedenstiema, G., Bylin, G. (1987). Ventilation-perfusion inequality in chronic asthma. Am. Rev. Respir. Dis., vol. 136, pp 605–612.

What is claimed is:

1. A device for determining one or more respiratory parameters relating to an individual, comprising a gas flow device having means for conducting a flow of inspiratory gas from an inlet opening to the respiratory system of the individual and a flow of expiratory gas from the respiratory system of the individual to an outlet opening, a gas-mixing unit for supplying a substantially homogeneous gas to the inlet opening of the gas flow device, first supply means for supplying a first gas to an inlet of the gas mixing unit and having first control means for controlling the flow of the first gas, second supply means for supplying a second gas having an oxygen fraction different to the gas supplied from the first supply means to an inlet of the gas mixing unit and having second control means for controlling the flow of the second gas, a computer for determining said one or more respiratory parameters, first detection means for detecting the level of oxygen ($SaO_2$, $SpO_2$, $PaO_2$, $PpO_2$) in the blood circulation of the individual and producing an output to the computer accordingly, and second detection means for detecting the level of oxygen ($FIO_2$, $FE'O_2$, $FEO_2$, $PIO_2$, $PE'O_2$, $PEO_2$) in the gas flow passing into or out of the respiratory system of the individual and producing an output to the computer accordingly, the computer being adapted for retrieving and storing at least two measurements being the concurrent output produced by the first detection means and the second detection means within a data structure, in which the two stored outputs are mutually related, in data storage associated with the computer, the at least two measurements being conducted at corresponding levels of oxygen in the gas flow passing into the respiratory system, the computer further being adapted for determining at least two respiratory parameter (Rdiff, shunt, $\dot{V}/\dot{Q}$, H-shift, V-shift) being descriptive of the pulmonary gas exchange of the individual, the determination being based on the at least two measurements.

2. A device according to claim 1, wherein said parameter(s) (Rdiff, shunt, $\dot{V}/\dot{Q}$, H-shift, V-shift) is/are generalised parameters being comparable to similar parameter(s) determined for other individuals.

3. A device according to claim 1, wherein the computer further is adapted for performing a procedure at least once, the procedure comprising
   determining, based on at least two measurements, whether additional measurements are required,
   asserting a possible desired target defining a desired output of the first detection means,
   producing a possible control data item based on the target, and
   retrieving and storing, in the data structure, additional measurement results being the concurrent output produced by the first detection means and the second detection means.

4. A device according to claim 1, wherein the second detection means are arranged for detecting the level (FIO2, PIO2) of oxygen in the gas flow passing into the respiratory system, and the device further comprises
   third detection means for detecting the level (FE'O2, FEO2, PE'O2, PEO2) of oxygen in the gas flow passing out of the respiratory system and producing an output to the computer accordingly, and
   fourth detection means for detecting variables (Vt, f, $\dot{V}$) of the gas flow passing the respiratory system and producing an output to the computer accordingly, said output being sufficient for the computer to establish the volume flow of gas passing the respiratory system,
   the computer being adapted for retrieving and storing output from the third detection means and the fourth detection means within the data structure relating these stored output mutually as well as with the output from the first detection means and the second detection means retrieved simultaneously.

5. A device according to claim 4, wherein the computer further being adapted for establishing, based on said measurement(s), the oxygen consumption ($VO_2$) of the individual.

6. A device according to claim 1, wherein the computer is adapted to determine a parameter relating to an equilibrium state of the overall oxygen uptake or consumption of the individual based on the output of at least one of the detection means, to compare said parameter with a predefined threshold value and to produce a control data item accordingly if said parameter exceeds said threshold value.

7. A device according to claim 1, wherein the computer is adapted to assess the appropriate change in oxygen level in the inspired gas (FIO2) from the current oxygen level (FIO2) so as to achieve a given desired target oxygen level in the blood (SaO2, SpO2, PaO2, PpO2) and produce a control data item accordingly.

8. A device according to claim 7, wherein the assessment of change in oxygen level in the inspired gas is based on a predefined set of data representing statistical distributions of parameters stored within data storage associated with the computer and on said measurements.

9. A device according to claim 7, wherein the assessment of change in oxygen level in the inspired gas is based on the rate of change of the output of at least one of the detection means in response to a change in oxygen level ($FIO_2$) in the inspired gas flow.

10. A device according to claim 7, wherein the computer is adapted to operate the control means for controlling the flow to the gas mixing unit of at least one gas, in response to said control data item relating to the assessed change in oxygen level from the computer so as to change the oxygen level (FIO2) in the inspired gas flow accordingly.

11. A device according to claim 1, wherein one gas is atmospheric air and another gas has an oxygen fraction higher than that of atmospheric air.

12. A device according to claim 11, wherein one gas is atmospheric air and another gas has an oxygen fraction higher than that of atmospheric air and in the range of 0.85 to 1.00.

13. A device according to claim 1, wherein one gas is atmospheric air and another gas has an oxygen fraction in the range of 0.00 to 0.21.

14. A device according to claim 13, wherein one gas is atmospheric air and another gas has an oxygen fraction in the range 0.00 to 0.05.

15. A device according to claim 1, wherein the oxygen saturation in the blood circulation of the individual is in the range of 65 to 100%.

16. A device according to claim 15, wherein the oxygen saturation in the blood circulation of the individual is in the range of 85 to 100%.

17. A device according to claim 1, wherein the first detection means is arranged for detecting a parameter relating to the saturation level of oxygen in the arterial blood stream.

18. A device for determining one or more respiratory parameters relating to an individual, comprising
   a gas flow device having means for conducting a flow of inspiratory gas from an inlet opening to the respiratory system of the individual and a flow of expiratory gas from the respiratory system of the individual to an outlet opening,
   a gas-mixing unit for supplying a substantially homogeneous gas to the inlet opening of the gas flow device,
   first supply means for supplying a first gas to an inlet of the gas mixing unit and having first control means for controlling the flow of the first gas,
   second supply means for supplying a second gas having an oxygen fraction different to the gas supplied from the first supply means to an inlet of the gas mixing unit and having second control means for controlling the flow of the second gas,
   a computer for determining said one or more respiratory parameters,
   first detection means for detecting the level of oxygen ($SaO_2$, $SpO_2$, $PaO_2$, $PpO_2$) in the blood circulation of the individual and producing an output to the computer accordingly, and
   second detection means for detecting the level of oxygen ($FIO_2$, $FE'O_2$, $FEO_2$, $PIO_2$, $PE'O_2$, $PEO_2$) in the gas flow passing into or out of the respiratory system of the individual and producing an output to the computer accordingly,
   the computer being adapted for retrieving and storing a first measurement being the concurrent output produced by the first detection means and the second detection means within a data structure, in which the two stored outputs are mutually related, in data storage associated with the computer, the computer being further adapted for performing a procedure at least once, the procedure comprising determining, based on data stored within the data structure, whether additional measurements are required, asserting a possible desired target defining a desired output of the first detection means, producing a possible control data item based on the target, and retrieving and storing, in the data structure, additional measurement results being the concurrent output produced by the first detection means and the second detection means.

19. A device according to claim 18, wherein the second detection means are arranged for detecting the level ($FIO_2$, $PIO_2$) of oxygen in the gas flow passing into the respiratory system, and the device further comprises third detection means for detecting the level ($FE'O_2$, $F\overline{E}O_2$, $PE'O_2$, $P\overline{E}O_2$) of oxygen in the gas flow passing out of the respiratory system and producing an output to the computer accordingly, and fourth detection means for detecting variables (Vt, f, $\dot{V}$) of the gas flow passing the respiratory system and producing an output to the computer accordingly, said output being sufficient for the computer to establish the volume flow of gas passing the respiratory system, the computer being adapted for retrieving and storing output from the third detection means and the fourth detection means within the data structure in data storage associated with the computer, in which the stored outputs are mutually related and related to the output from the first detection means and the second detection means, and the output from the four detection means can be retrieved simultaneously.

20. A device according to claim 19, wherein the computer further being adapted for establishing, based on said measurement(s), the oxygen consumption ($VO_2$) of the individual.

21. A device according to claim 18, wherein the computer is adapted for determining at least one respiratory parameter (Rdiff, shunt, $\dot{V}/\dot{Q}$, H-shift, V-shift) being descriptive of the condition of the individual, the determination being based on at least two measurements.

22. A device according to claim 21, wherein at least two respiratory parameters (Rdiff, shunt, $\dot{V}/\dot{Q}$, H-shift, V-shift) are determined.

23. A device according to claim 21, wherein said parameter(s) (Rdiff, shunt, $\dot{V}/\dot{Q}$, H-shift, V-shift) is/are generalised parameters being comparable to similar parameter(s) determined for other individuals.

24. A device according to claim 18, wherein the computer is adapted to determine a parameter relating to an equilibrium state of the overall oxygen uptake or consumption of the individual based on the output of at least one of the detection means, to compare said parameter with a predefined threshold value and to produce a control data item accordingly if said parameter exceeds said threshold value.

25. A device according to claim 18, wherein the computer is adapted to assess the appropriate change in oxygen level in the inspired gas (FIO2) from the current oxygen level (FIO2) so as to achieve a given desired target oxygen level in the blood (SaO2, SpO2, PaO2, PpO2) and produce a control data item accordingly.

26. A device according to claim 25, wherein the assessment of change in oxygen level in the inspired gas is based on a predefined set of data representing statistical distributions of parameters stored within data storage means associated with the computer and on said measurement(s).

27. A device according to claim 25, wherein the assessment of change in oxygen level in the inspired gas is based on the rate of change of the output of at least one of the detection means in response to a change in oxygen level ($FIO_2$) in the inspired gas flow.

28. A device according to claim 25, wherein the computer is adapted to operate the control means for controlling the flow to the gas mixing unit of at least one gas, in response to said control data item relating to the assessed change in oxygen level from the computer so as to change the oxygen level (FIO2) in the inspired gas flow accordingly.

29. A device according to claim 18, wherein one gas is atmospheric air and another gas has an oxygen fraction higher than that of atmospheric air.

30. A device according to claim 29, wherein one gas is atmospheric air and another gas has an oxygen fraction higher than that of atmospheric air and in the range 0.85 to 1.00.

31. A device according to claim 18, wherein one gas is atmospheric air and another gas has an oxygen fraction in the range of 0.00 to 0.21.

32. A device according to claim 31, wherein one gas is atmospheric air and another gas has an oxygen fraction in the range of 0.00 to 0.05.

33. A device according to claim 18, wherein the oxygen saturation in the blood circulation of the individual is in the range of 65 to 100%.

34. A device according to claim 33, wherein the oxygen saturation in the blood circulation of the individual is in the range of 85 to 100%.

35. A device according to claim 18, wherein the first detection means is arranged for detecting a parameter relating to the saturation level of oxygen in the arterial blood stream.

36. A device for determining one or more respiratory parameters relating to an individual, comprising a gas flow device having means for conducting a flow of inspiratory gas from an inlet opening to the respiratory system of the individual and a flow of expiratory gas from the respiratory system of the individual to an outlet opening, a gas-mixing unit for supplying a substantially homogeneous gas to the inlet opening of the gas flow device, first supply means for supplying a first gas to an inlet of the gas mixing unit and having first control means for controlling the flow of the first gas, second supply means for supplying a second gas having an oxygen fraction different to the gas supplied from the first supply means to an inlet of the gas mixing unit and having second control means for controlling the flow of the second gas, a computer for determining said one or more respiratory parameters, first detection means for detecting the level of oxygen ($SaO_2$, $SpO_2$, $PaO_2$, $PpO_2$) in the blood circulation of the individual and producing an output to the computer accordingly, and second detection means for detecting the level of oxygen ($FIO_2$, $FE'O_2$, $F\overline{E}O_2$, $PIO_2$, $PE'O_2$, $F\overline{E}O_2$) in the gas flow passing into or out of the respiratory system of the individual and producing an output to the computer accordingly, the computer being adapted for retrieving and storing at least a first measurement being the concurrent output produced by the first detection means and the second detection means within a data structure, in which the two stored outputs are mutually related, in data storage associated with the computer, the computer further being adapted to assess the appropriate change in oxygen level in the inspired gas ($FIO_2$) from the current oxygen level ($FIO_2$) so as to achieve a given desired target oxygen level in the blood ($SaO_2$, $SpO_2$, $PaO_2$, $PpO_2$) and produce a control data item accordingly, wherein the assessment of change in oxygen level in the inspired gas is based on a predefined set of data representing statistical distributions of parameters stored within data storage means associated with the computer and on said measurement(s).

37. A device according to claim 36, wherein the assessment of change in oxygen level in the inspired gas is based on the rate of change of the output of at least one of the detection means in response to a change in oxygen level ($FIO_2$) in the inspired gas flow.

38. A device according to claim 36, wherein the computer is adapted to operate the control means for controlling the flow to the gas mixing unit of at least one gas, in response to said control data item from the computer so as to change the oxygen level (FIO2) in the inspired gas flow accordingly.

39. A device according to claim 36, wherein the computer further is adapted for performing a procedure at least once, the procedure comprising determining, based on at least one measurement, whether additional measurements are required, asserting a possible desired target defining a desired output of the first detection means, producing a possible control data item based on the target, and retrieving and storing, in the data structure, additional measurement results being the concurrent output produced by the first detection means and the second detection means.

40. A device according to claim 36, wherein the second detection means are arranged for detecting the level (FIO2, PIO2) of oxygen in the gas flow passing into the respiratory system, and the device further comprises third detection means for detecting the level (FE'O2, F EO$_2$, PE'O2, PEO2) of oxygen in the gas flow passing out of the respiratory system and producing an output to the computer accordingly, and fourth detection means for detecting variables (Vt, f, $\dot{V}$) of the gas flow passing the respiratory system and producing an output to the computer accordingly, said output being sufficient for the computer to establish the volume flow of gas passing the respiratory system, the computer being adapted for retrieving and storing output from the third detection means and the fourth detection means within the data structure relating these stored output mutually as well as with the output from the first detection means and the second detection means retrieved simultaneously.

41. A device according to claim 40, wherein the computer further being adapted for establishing, based on said measurement(s), the oxygen consumption ($VO_2$) of the individual.

42. A device according to claim 36, wherein the computer is adapted for determining at least one respiratory parameter (Rdiff, shunt, $\dot{V}/\dot{Q}$, H-shift, V-shift) being descriptive of the condition of the individual, the determination being based on at least two measurements.

43. A device according to claim 42, wherein at least two respiratory parameters (Rdiff, shunt, $\dot{V}/\dot{Q}$, H-shift, V-shift) are determined.

44. A device according to claim 42, wherein said parameter(s) (Rdiff, shunt, $\dot{V}/\dot{Q}$, H-shift, V-shift) is/are generalized parameters being comparable to similar parameter(s) determined for other individuals.

45. A device according to claim 36, wherein the computer is adapted to determine a parameter relating to an equilibrium state of the overall oxygen uptake or consumption of the individual based on the output of at least one of the detection means, to compare said parameter with a predefined threshold value and to produce a control data item accordingly if said parameter exceeds said threshold value.

46. A device according to claim 36, wherein one gas is atmospheric air and another gas has an oxygen fraction higher than that of atmospheric air.

47. A device according to claim 36, wherein one gas is atmospheric air and another gas has an oxygen fraction in the range of 0.00 to 0.21.

48. A device according to claim 36, wherein the oxygen saturation in the blood circulation of the individual is in the range of 65 to 100%.

49. A device according to claim 36, wherein the first detection means is arranged for detecting a parameter relating to the saturation level of oxygen in the arterial blood stream.

50. Method for determining one or more respiratory parameters using a device according to claim 36, wherein the individual is an apparently healthy individual.

51. Method for determining one or more respiratory parameters using a device according to claim 36, wherein the individual is considered to have a risk of suffering from hypoxemia.

52. Method for determining one or more respiratory parameters using a device according to claim 36, wherein the individual is suffering from hypoxemia.

53. Method according to claim 52, wherein the individual is suffering from one or more disease(s) selected from the group(s) comprising left sided heart failure, adult respiratory distress syndrome, pneumonia, postoperative hypoxemia, pulmonary fibrosis, toxic pulmonary lymphoedema, pulmonary embolisms, chronic obstructive pulmonary disease and cardiac shunting.

54. A device according to claim 36, wherein one gas is atmospheric air and another gas has an oxygen fraction higher than that of atmospheric air and in the range of 0.85 to 1.00.

55. A device according to claim 36, wherein one gas is atmospheric air and another gas has an oxygen fraction in the range of 0.00 to 0.05.

56. A device according to claim 36, wherein the oxygen saturation in the blood circulation of the individual is in the range of 85 to 100%.

57. A computer system comprising at least one general purpose computer having one or more computer programs stored within data storage means associated therewith, the computer system being arranged for as well as being adapted for determining one or more respiratory parameters relating to an individual, the computer system being intended for use with an associated gas flow device having means for conducting a flow of inspiratory gas from an inlet opening to the respiratory system of the individual and a flow of expiratory gas from the respiratory system of the individual to an outlet opening, an associated gas-mixing unit for supplying a substantially homogeneous gas to the inlet opening of the gas flow device, associated first supply means for supplying a first gas to an inlet of the gas mixing unit and having first control means for controlling the flow of the first gas, associated second supply means for supplying a second gas having an oxygen fraction different to the gas supplied from the first supply means to an inlet of the gas mixing unit and having second control means for controlling the flow of the second gas, associated first detection means for detecting the level of oxygen ($SaO_2$, $SpO_2$, $PaO_2$, $PpO_2$) in the blood circulation of the individual and producing an output to the computer system accordingly, and associated second detection means for detecting the level of oxygen ($FIO_2$, $FE'O_2$, $F\overline{E}O_2$, $PIO_2$, $PE'O_2$, $P\overline{E}O_2$) in the gas flow passing into or out of the respiratory system of the individual and producing an output to the computer system accordingly, the computer system being adapted for retrieving and storing at least two measurements being the concurrent output produced by the first detection means and the second detection means within a data structure, in which the two stored outputs are mutually related, in data storage associated with the computer system, the at least two measurements being conducted at corresponding levels of oxygen in the gas flow passing into the respiratory system, the computer system further being adapted for determining at least two respiratory parameters (Rdiff, shunt, $\dot{V}/\dot{Q}$, H-shift, V-shift) being descriptive of the pulmonary gas exchange of the individual, the determination being based on the at least two measurements.

58. A computer program product embodied on a computer readable medium being adapted to enable a computer system according to claim 57 to determine one or more respiratory parameters of an individual.

\* \* \* \* \*